(12) United States Patent
Chen et al.

(10) Patent No.: US 11,993,555 B2
(45) Date of Patent: May 28, 2024

(54) CONJUGATED TRIENE COMPOUND, AND PREPARATION AND APPLICATION THEREOF

(71) Applicant: ORIENTAL(LUZHOU) AGROCHEMICALS CO., LTD., Sichuan (CN)

(72) Inventors: Bangchi Chen, Sichuan (CN); Yinwei Sun, Sichuan (CN); Zhongyuan Wang, Sichuan (CN); Teng Lai, Sichuan (CN)

(73) Assignee: ORIENTAL(LUZHOU) AGROCHEMICALS CO., LTD., Luzhou (CN)

(*) Notice: Subject to any disclaimer, the term of this patent is extended or adjusted under 35 U.S.C. 154(b) by 497 days.

(21) Appl. No.: 17/489,654

(22) Filed: Sep. 29, 2021

(65) Prior Publication Data
US 2022/0024861 A1 Jan. 27, 2022

Related U.S. Application Data

(63) Continuation of application No. PCT/CN2019/080824, filed on Apr. 1, 2019.

(51) Int. Cl.
*C07C 255/31* (2006.01)
*C07C 231/06* (2006.01)
*C07C 253/30* (2006.01)
*C07D 491/044* (2006.01)

(52) U.S. Cl.
CPC .......... *C07C 255/31* (2013.01); *C07C 231/06* (2013.01); *C07C 253/30* (2013.01); *C07D 491/044* (2013.01); *C07C 2601/16* (2017.05)

(58) Field of Classification Search
CPC ... C07C 255/31; C07C 231/06; C07C 253/30; C07D 491/044
See application file for complete search history.

(56) References Cited

U.S. PATENT DOCUMENTS

| 4,293,626 A | 10/1981 | Webster et al. |
| 11,345,648 B2 * | 5/2022 | Chen .................. C07C 253/30 |

FOREIGN PATENT DOCUMENTS

| CN | 108264469 A | 7/2018 |
| JP | H04338761 A | 11/1992 |
| WO | 9947525 A1 | 9/1999 |
| WO | 0117352 A1 | 3/2001 |
| WO | 2007073933 A2 | 7/2007 |
| WO | 2008049618 A2 | 5/2008 |

* cited by examiner

*Primary Examiner* — Sikarl A Witherspoon

(57) ABSTRACT

Disclosed are a type of conjugated triene compounds (1), and a preparation and application thereof. In this method, a 2-(cyclohexenylidene)malonic acid derivative is sequentially subjected to isomerization, halogenation reaction in the presence of a halogenating agent and dehydrohalogenation to prepare the conjugated triene compounds (1). This disclosure further provides a method of preparing a 2-aryl malonic acid derivative from the conjugated triene compounds (1) through aromatization reaction.

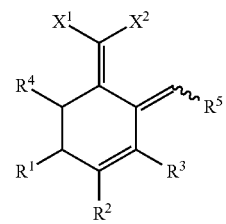

12 Claims, No Drawings

CONJUGATED TRIENE COMPOUND, AND PREPARATION AND APPLICATION THEREOF

CROSS-REFERENCE TO RELATED APPLICATIONS

This application is a continuation of International Patent Application No. PCT/CN2019/080824, filed on Apr. 1, 2019. The content of the aforementioned application, including any intervening amendments thereto, is incorporated herein by reference in its entirety.

TECHNICAL FIELD

This application relates to organic synthesis, and more specifically to a conjugated triene compound, and a preparation and application thereof.

BACKGROUND

Provided herein is a type of novel conjugated triene compounds of formula (1),

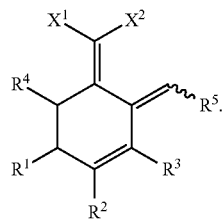

Compounds (1) with multifunctional groups, after further functional group transformations are expected to be useful in the synthesis of a variety of derivatives with different chemical properties, physical properties, and biological activities, these derivatives can be used to produce final products with practical application values, such as the herbicide [8-(2,6-diethyl-4-methylphenyl)-7-oxo-1,2,4,5-tetrahydro-7H-pyrazolo[1,2-d][1,4,5]oxadiazepin-9-yl] 2,2-dimethylpropanoate (Pinoxaden). The application of this herbicide has been disclosed by International Patent Publication Nos. WO 9947525, WO 0117352, WO 2007073933 and WO 2008049618.

However, these structurally novel compounds (1) have not been reported yet.

SUMMARY

A first object of this application is to provide a conjugated triene compound of formula (1)

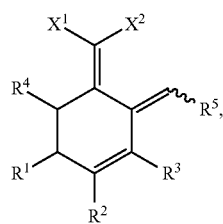

wherein:
$R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen and sulfur; and
$X^1$ and $X^2$ each are independently a cyano group or —$COR^6$ where $R^6$ is hydrogen, a $C_1$-$C_{10}$ alkyl group, a wherein $R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen and sulfur; and
$X^1$ and $X^2$ each are independently a cyano group or —$COR^6$ where $R^6$ is hydrogen, a $C_1$-$C_{10}$ alkyl group, a $C_1$-$C_{10}$ alkoxy group, a $C_6$-$C_{12}$ aryloxy group, an amino group, a $C_1$-$C_{10}$ alkyl amino group, a $C_6$-$C_{12}$ arylamino group, a di($C_1$-$C_{10}$ alkyl)amino group, a ($C_1$-$C_{10}$ alkyl)($C_6$-$C_{12}$ aryl)amino group, a di($C_6$-$C_{12}$ aryl)amino group, a $C_6$-$C_{12}$ aryl group or a heteroaryl group containing one or two atoms selected from nitrogen, oxygen and sulfur.

In an embodiment, $R^1$, $R^2$, $R^3$, $R^4$ and $R^5$ each are independently hydrogen, a $C_1$-$C_4$ alkyl group or a $C_6$-$C_{12}$ aryl group.

In an embodiment, $R^1$ and $R^3$ are hydrogen; $R^2$ and $R^5$ are a methyl group; and $R^4$ is an ethyl group.

In an embodiment, $X^1$ and $X^2$ each are independently a cyano group, —COOMe, —COOEt or —$CONH_2$.

A second object of this application is to provide a method for preparing the conjugated triene compound of formula (1), comprising:
subjecting compound (2) to isomerization to produce compound (3); and
subjecting the compound (3) to halogenation in the presence of a halogenating agent and dehydrohalogenation to produce the conjugated triene compound of formula (1), as shown in the following reaction scheme:

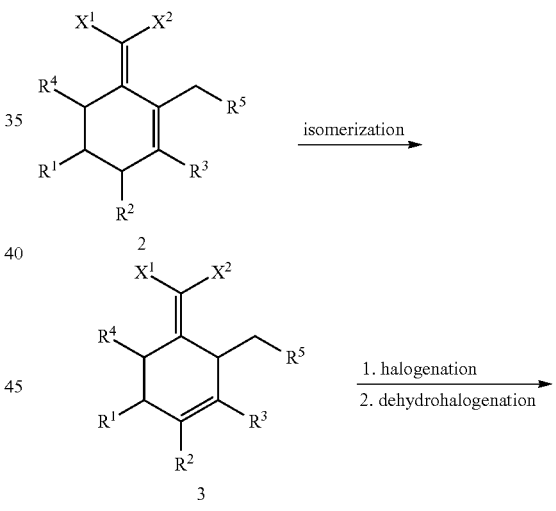

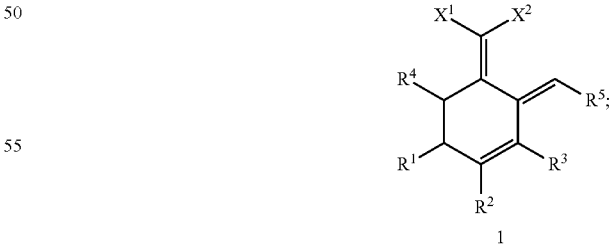

$C_1$-$C_{10}$ alkoxy group, a $C_6$-$C_{12}$ aryloxy group, an amino group, a $C_1$-$C_{10}$ alkylamino group, a $C_6$-$C_{12}$ arylamino group, a di($C_1$-$C_{10}$ alkyl)amino group, a ($C_1$-$C_{10}$ alkyl)($C_6$-$C_{12}$ aryl)amino group, a di($C_6$-$C_{12}$ aryl)amino group, a $C_6$-$C_{12}$ aryl group or a heteroaryl group containing one or two atoms selected from nitrogen, oxygen and sulfur.

In an embodiment, $R^1$, $R^2$, $R^3$, $R^4$ and $R^5$ each are independently hydrogen, a $C_1$-$C_4$ alkyl group or a $C_6$-$C_{12}$ aryl group.

In an embodiment, $X^1$ and $X^2$ each are independently a cyano group, —COOMe, —COOEt or —CONH$_2$.

In an embodiment, the isomerization is carried out in the presence of a base A, where the base A is selected from the group consisting of an alkali metal hydroxide, an alkali metal alcoholate, an alkali metal hydride, an alkaline earth metal hydroxide, an alkaline earth metal alcoholate, an alkaline earth metal hydride and a mixture thereof, and a molar ratio of the base A to the compound (2) is (0.8-2.4):1, preferably (1.0-1.2):1.

In an embodiment, the halogenating agent is selected from the group consisting of an elemental halogen (such as chlorine gas and liquid bromine), a hypohalous acid (such as hypochlorous acid and hypobromous acid), a sulfonyl halide (such as a sulfuryl chloride), a thionyl halide (such as thionyl chloride) and a mixture thereof, preferably chlorine gas, sulfuryl chloride or liquid bromine.

In an embodiment, the dehydrohalogenation is performed at 0-100° C., preferably 50-80° C.

In an embodiment, the dehydrohalogenation is carried out in the presence of a base B, where the base B is an inorganic base or an organic base, preferably an organic base, and more preferably an organic amine. In an embodiment, the base B is triethylamine.

In an embodiment, the compound (1) is prepared from the compound (2) in a stepwise manner or a one-pot manner.

A third object of this application is to provide a method of preparing a 2-aryl malonic acid derivative (4), comprising:
aromatizing compound (1) to produce the 2-arylmalonic acid derivative (4), as shown in the following reaction scheme:

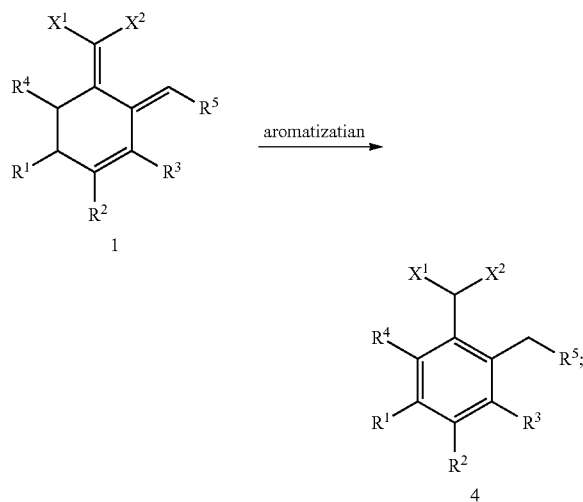

wherein:
$R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen or sulfur; and $X^1$ and $X^2$ each are independently a cyano group or —COR$^6$ where $R^6$ is hydrogen, a $C_1$-$C_{10}$ alkyl group, a $C_1$-$C_{10}$ alkoxy group, a $C_6$-$C_{12}$ aryloxy group, an amino group, a $C_1$-$C_{10}$ alkylamino group, a $C_6$-$C_{12}$ arylamino group, a di($C_1$-$C_{10}$ alkyl)amino group, a ($C_1$-$C_{10}$ alkyl)($C_6$-$C_{12}$ aryl)amino group, a di($C_6$-$C_{12}$ aryl)amino group, a $C_6$-$C_{12}$ aryl group or a heteroaryl group containing one or two atoms selected from nitrogen, oxygen and sulfur.

In an embodiment, $R^1$, $R^2$, $R^3$, $R^4$ and $R^5$ each are independently hydrogen, a $C_1$-$C_4$ alkyl group or a $C_6$-$C_{12}$ aryl group.

In an embodiment, $X^1$ and $X^2$ each are independently a cyano group, —COOMe, —COOEt or —CONH$_2$.

In an embodiment, an aromatization temperature is 100-150° C., preferably 110-150° C.

In an embodiment, the aromatization reaction is carried out in the presence of a catalyst, where the catalyst is selected from the group consisting of an alkali metal halide, an alkaline earth metal and a mixture thereof, preferably lithium chloride or sodium chloride; and a molar ratio of the catalyst to the compound (1) is (0.005-2.4):1.

The inventors of the present invention have also found that it is not necessary to separate the intermediate produced in the preparation of the compound (1), and the 2-aryl malonic acid derivative (4) can be directly obtained in a one-pot manner.

In an embodiment, 2-(6-ethyl-2-ethylidene-4-methyl-3-ene-1-cyclohexylidene) malononitrile (namely, $R^1$ and $R^3$ are hydrogen; $R^2$ and $R^5$ are methyl; $R^4$ is ethyl; and $X^1$ and $X^2$ are cyano) and/or 2-(2,6-diethyl-4-methylphenyl) malononitrile (namely, $R^1$ and $R^3$ are hydrogen; $R^2$ and $R^5$ are methyl; $R^4$ is ethyl; and $X^1$ and $X^2$ are cyano) produced by the method provided herein can undergo further conversion and reaction to prepare the herbicide 2,2-dimethyl-,8-(2,6-diethyl-4-methylphenyl)-1,2,4,5-tetrahydro-7-oxo-7H-pyrazolo[1,2-d][1,4,5]oxadiazepin-9-yl ester (Pinoxaden).

Compared to the prior art, this application has the following beneficial effects.
(1) This application provides a type of structurally novel conjugated triene compounds (1) and a preparation method thereof.
(2) The conjugated triene compounds (1) containing multi-functional groups can be used to synthesize other valuable compounds through further functional group transformations, such as the herbicide 2,2-dimethyl-,8-(2,6-diethyl-4-methylphenyl)-1,2,4,5-tetrahydro-7-oxo-7H-pyrazolo[1,2-d][1,4,5]oxadiazepin-9-yl ester (Pinoxaden).

DETAILED DESCRIPTION OF EMBODIMENTS

This application will be described in detail below with reference to the embodiments to make objects, technical features and advantages of this application clearer, but these embodiments are not intended to limit the scope of this application.

The starting material 2 can be prepared by known methods in the prior art (for example, WO 2018/120094).

Example 1: Preparation of 2-(2,6-diethyl-4-methyl-3-ene-1-cyclohexylidene) Malononitrile To a 250 mL three-necked flask equipped with a magnetic stirrer and a thermometer were sequentially added 85.0 g of methanol and 42.9 g of 2-(2,6-diethyl-4-methyl-2-ene-1-cyclohexylidene) malononitrile. The reaction mixture was mixed, heated to 50° C., and 10.8 g of sodium methoxide was added. Then the reaction mixture was stirred for 5 min, and cooled, acidificated, extracted, concentrated and separated to give 39.0 g of 2-(2,6-diethyl-4-methyl-3-ene-1-cyclohexylidene) malononitrile.

$^1$HNMR (CDCl$_3$, 500 MHz, TMS): δ 5.41 (m, 1H), 3.23 (m, 1H), 3.12 (q, J=7.5 Hz, 1H), 2.40-2.35 (m, 1H), 2.15 (d, J=17.5 Hz, 1H), 1.73 (d, J=1.5 Hz, 3H), 1.68-1.59 (m, 4H), 1.13 (t, J=7.5 Hz, 3H), 0.95 (t, J=7.6 Hz, 3H).

$^{13}$CNMR (CDCl3, 125 MHz): δ 189.5, 131.7, 119.0, 111.9, 111.7, 84.8, 44.0, 43.0, 35.9, 30.5, 27.4, 23.3, 12.8, 12.2.

Example 2: Preparation of 2-(2,6-diethyl-4-methyl-3-ene-1-cyclohexylidene) Malononitrile To a 250 mL three-necked flask equipped with a magnetic stirrer and a thermometer were sequentially added 85.0 g of tetrahydrofuran and 42.9 g of 2-(2,6-diethyl-4-methyl-2-ene-1-cyclohexylidene) malononitrile. The reaction mixture was mixed, heated to 50° C., and 11.22 g of potassium hydroxide was added. Then the reaction mixture was stirred for 30 min, and cooled, acidificated, extracted, concentrated and separated to give 36.9 g of 2-(2,6-diethyl-4-methyl-3-ene-1-cyclohexylidene) malononitrile.

Example 3: Preparation of 2-(6-ethyl-2-ethylidene-4-methyl-3-ene-1-cyclohexylidene) Malononitrile To a 500 mL three-necked flask equipped with a magnetic stirrer and a thermometer were sequentially added 170.0 g of acetic acid and 42.9 g of 2-(2,6-diethyl-4-methyl-3-ene-1-cyclohexylidene) malononitrile prepared by the method provided in Example 1. The reaction mixture was mixed, heated to 45° C., and 29.8 g of sulfonyl chloride was added. Then the reaction mixture was reacted at 45° C. for 1 h, concentrated, 200 mL of N,N-dimethylformamide was added and heated to 50° C. until the reaction was complete. The reaction mixture was cooled to room temperature, and extracted, washed, concentrated and separated to give 34.0 g of 2-(6-ethyl-2-ethylidene-4-methyl-3-ene-1-cyclohexylidene) malononitrile.

$^1$HNMR (CDCl$_3$, 500 MHz, TMS): δ 6.22 (q, J=7.5 Hz, 1H), 6.11 (s, 1H), 3.13-3.08 (m, 1H), 2.61-2.56 (m, 1H), 2.43 (d, J=17.5 Hz, 1H), 1.92 (d, J=7.5 Hz, 3H), 1.83 (s, 3H), 1.57-1.49 (m, 2H), 0.86 (t, J=7.0 Hz, 3H).

$^{13}$CNMR (CDCl$_3$, 125 MHz): δ 180.77, 136.10, 130.43, 130.15, 117.07, 112.94, 112.90, 79.53, 43.45, 37.74, 26.62, 23.29, 13.64, 11.39.

Example 4: Preparation of 2-(6-ethyl-2-ethylidene-4-methyl-3-ene-1-cyclohexylidene) Malononitrile To a 500 mL three-necked flask equipped with a magnetic stirrer and a thermometer were sequentially added 125.0 g of N,N-dimethylformamide and 64.4 g of 2-(2,6-diethyl-4-methyl-3-ene-1-cyclohexylidene) malononitrile prepared by the method provided in Example 1. The reaction mixture was mixed, cooled to 0° C., and fed with chlorine gas until the reaction was completed. Then the reaction mixture was concentrated, 300 mL of N-methyl-pyrrolidone was added and heated to 70° C. until the reaction was complete. The reaction mixture was cooled to room temperature, and then extracted, washed, concentrated and separated to give 53.5 g of 2-(6-ethyl-2-ethylidene-4-methyl-3-ene-1-cyclohexylidene) malononitrile.

Example 5: Preparation of 2-(6-ethyl-2-ethylidene-4-methyl-3-ene-1-cyclohexylidene) Malononitrile To a 250 mL three-necked flask equipped with a magnetic stirrer and a thermometer were sequentially added 125.0 g of chlorobenzene and 64.4 g of 2-(2,6-diethyl-4-methyl-2-ene-1-cyclohexylidene) malononitrile. The reaction mixture was mixed, cooled to 0° C., and then introduced with chlorine gas until the reaction was completed. The reaction mixture was concentrated, and 300 mL of N-methyl-pyrrolidone was added and heated to 80° C. until the reaction was complete. The reaction mixture was cooled, extracted, washed, concentrated and separated to give 50.9 g of 2-(6-ethyl-2-ethylidene-4-methyl-3-ene-1-cyclohexylidene) malononitrile.

Example 6: Preparation of 2-(6-ethyl-2-ethylidene-4-methyl-3-ene-1-cyclohexylidene) Malononitrile To a 250 mL three-necked flask equipped with a magnetic stirrer and a thermometer were sequentially added 85.0 g of tetrahydrofuran and 42.9 g of 2-(2,6-diethyl-4-methyl-2-ene-1-cyclohexylidene) malononitrile. The reaction mixture was mixed, heated to 50° C., and 8.0 g of sodium hydroxide was added. Then the reaction mixture was stirred for 5 min, cooled to room temperature, 32.7 g of a 5% sodium hypochlorite solution was added and then 10% hydrochloric acid solution was slowly dropwise added to adjust a pH to 3-4. The reaction mixture was stirred at room temperature for 30 min and ethyl acetate was added. The organic phase was collected, washed, dried, concentrated, 30.4 g of triethylamine and 200 mL of toluene were added, and heated to 70° C. until the reaction was completed. The reaction mixture was cooled, acidified, washed, concentrated and separated to give 30.1 g of 2-(6-ethyl-2-ethylidene-4-methyl-3-ene-1-cyclohexylidene) malononitrile.

Example 7: Preparation of 2-(6-ethyl-2-ethylidene-4-methyl-3-ene-1-cyclohexylidene) Malononitrile To a 250 mL three-necked flask equipped with a magnetic stirrer and a thermometer were sequentially added 43.0 g of ethyl acetate and 21.5 g of 2-(2,6-diethyl-4-methyl-2-ene-1-cyclohexylidene) malononitrile. The reaction mixture was mixed, heated to 50° C., and 5.4 g of sodium methoxide was added. The reaction mixture was stirred for 5 min, cooled to −10° C., and introduced with chlorine gas until the reaction was completed. The reaction mixture was concentrated, 150 mL of N,N-dimethylformamide was added and heated to 80° C. until the reaction was complete. The reaction mixture was cooled, extracted, washed, concentrated and separated to give 18.9 g of 2-(6-ethyl-2-ethylidene-4-methyl-3-ene-1-cyclohexylidene) malononitrile.

Example 8: Preparation of 2-(6-ethyl-2-ethylidene-4-methyl-3-ene-1-cyclohexylidene) Malononitrile To a 500 mL three-necked flask equipped with a magnetic stirrer and a thermometer were sequentially added 170.0 g of acetic acid and 43.0 g of 2-(2,6-diethyl-4-methyl-2-ene-1-cyclohexylidene) malononitrile. The reaction mixture was mixed, heated to 40° C., and 29.8 g of sulfonyl chloride was added. The reaction mixture was reacted at 40° C. for 1 h, concentrated, 200 mL of N,N-dimethylformamide was added and heated to 70° C. until the reaction was complete. The reaction mixture was cooled, extracted, washed, concentrated and separated to give 28.0 g of 2-(6-ethyl-2-ethylidene-4-methyl-3-ene-1-cyclohexylidene) malononitrile.

Example 9: Preparation of 2-(2,6-diethyl-4-methylphenyl) Malononitrile

To a 250 mL three-necked flask equipped with a magnetic stirrer, a thermometer and a reflux condenser were sequentially added 125.0 g of chlorobenzene and 53.5 g of 2-(2,6-diethyl-4-methyl-3-ene-1-cyclohexylidene) malononitrile. The reaction mixture was mixed, cooled to 0° C., and introduced with chlorine gas until the reaction was completed. The reaction mixture was concentrated, and then 200 mL of N,N-dimethylformamide and 0.42 g of lithium chloride were sequentially added. The reaction mixture was refluxed until the reaction was complete, and was cooled, extracted, washed, concentrated and separated to give 47.8 g of 2-(2,6-diethyl-4-methylphenyl) malononitrile.

Example 10: Preparation of 2-(2,6-diethyl-4-methylphenyl) Malononitrile

To a 250 mL three-necked flask equipped with a magnetic stirrer, a thermometer and a reflux condenser were sequentially added 85.0 g of acetic acid and 21.5 g of 2-(2,6-diethyl-4-methyl-2-ene-1-cyclohexylidene) malononitrile. The reaction mixture was mixed, heated to 45° C., and 60 g of an acetic acid solution containing 17.6 g of liquid bromine were dropwise added. Then the reaction mixture was reacted at 45° C. for 2 h and concentrated, and then 100 mL of N,N-dimethylformamide and 0.95 g of lithium bromide were sequentially added, and refluxed until the reaction was complete. The reaction mixture was cooled, extracted, washed, concentrated and separated to give 10.6 g of 2-(2,6-diethyl-4-methylphenyl) malononitrile.

Example 11: Preparation of Methyl 2-cyano-2-(2,6-diethyl-4-methylphenyl) Acetate To a 250 mL three-necked flask equipped with a magnetic stirrer, a thermometer and a reflux condenser were sequentially added 60.0 g of ethyl acetate and 30.0 g of methyl 2-cyano-2-(2,6-diethyl-4-methyl-2-ene-1-cyclohexylidene) acetate. The reaction mixture was mixed, cooled to 5° C., and injected with chlorine gas until the reaction was completed. The reaction mixture was concentrated, and 100 mL of N,N-dimethylformamide and 0.22 g of lithium chloride were sequentially added, and refluxed until the reaction was complete. The reaction mixture was cooled, extracted, washed, concentrated and separated to give 24.0 g of methyl 2-cyano-2-(2,6-diethyl-4-methylphenyl) acetate.

$^1$HNMR (CDCl$_3$, 500 MHz, TMS): 6.95 (s, 2H), 3.80 (s, 3H), 2.76-2.59 (m, 4H), 2.32 (s, 3H), 1.24 (t, J=9.5 Hz, 6H).
$^{13}$C NMR (CDCl$_3$, 125 MHz): 166.5, 142.8, 139.2, 128.2, 123.9, 115.9, 53.7, 36.8, 26.3, 21.1, 15.0.

Example 12: Preparation of 2-(2,6-diethyl-4-methylphenyl) Malononitrile

To a 500 mL three-necked flask equipped with a magnetic stirrer, a thermometer and a reflux condenser were sequentially added 170.0 g of tetrahydrofuran and 42.9 g of 2-(2,6-diethyl-4-methyl-2-ene-1-cyclohexylidene) malononitrile. The reaction mixture was mixed, cooled to 5° C., 10.8 g of sodium methoxide was added and stirred for 30 min. Then the reaction mixture was heated to room temperature, 29.8 g of sulfonyl chloride was dropwise added and reacted at room temperature for 1 h. The reaction mixture was concentrated, and 200 mL of N,N-dimethylformamide and 0.42 g of lithium chloride were sequentially added and refluxed until the reaction was complete. The reaction mixture was cooled, extracted, washed, and separated to give 32.3 g of 2-(2,6-diethyl-4-methylphenyl) malononitrile.

Example 13: Preparation of 2-(2,6-diethyl-4-methylphenyl) Malononitrile

To a 500 mL three-necked flask equipped with a magnetic stirrer, a thermometer and a reflux condenser were sequentially added 125.0 g of chlorobenzene and 53.5 g of 2-(2,6-diethyl-4-methyl-2-ene-1-cyclohexylidene) malononitrile. The reaction mixture was mixed, cooled to 0° C., and injected with chlorine gas until the reaction was completed. The reaction mixture was concentrated, and 200 mL of N,N-dimethylformamide and 0.58 g of sodium chloride were sequentially added, and refluxed until the reaction was complete. The reaction mixture was cooled, extracted, washed, concentrated and separated to give 45.1 g of 2-(2,6-diethyl-4-methylphenyl) malononitrile.

Example 14: Preparation of 2-(2,6-diethyl-4-methylphenyl) Malononitrile

To a 250 mL three-necked flask equipped with a magnetic stirrer, a thermometer and a reflux condenser were sequentially added 150.0 g of N,N-dimethylformamide and 30.0 g of 2-(6-ethyl-2-ethylidene-4-methyl-3-ene-1-cyclohexylidene) malononitrile. The reaction mixture was mixed, heated to 130° C. in a nitrogen atmosphere and reacted. After the reaction was completed, the reaction mixture was cooled to room temperature, and extracted, washed, concentrated and separated to give 28.0 g of 2-(2, 6-diethyl-4-methylphenyl) malononitrile.

$^1$H NMR (CDCl$_3$, 500 MHz, TMS): δ 7.00 (s, 2H), 5.29 (s, 1H), 2.81 (q, J=7.5 Hz, 4H), 2.34 (s, 3H), 1.32 (t, J=7.5 Hz, 6H).
$^{13}$C NMR (CDCl$_3$, 125 MHz): δ 142.66, 140.73, 128.74, 120.00, 112.24, 26.48, 21.21, 21.13, 15.03.

Example 15: Preparation of 2-(2,6-diethyl-4-methylphenyl) Malonamide

To a 100 mL three-necked flask equipped with a magnetic stirrer and a thermometer were sequentially added 3.6 g of water and 50.0 g of concentrated sulfuric acid. The reaction mixture was mixed and heated to 45° C., and 21.2 g of 2-(2,6-diethyl-4-methylphenyl) malononitrile prepared in Example 13 was slowly added. The reaction mixture was reacted at 50° C. under stirring for 5 h. After the reaction was completed, the reaction mixture was cooled, poured into ice water, and subjected to extraction with ethyl acetate. The organic phases were combined, dried and concentrated to give 24.1 g of 2-(2,6-diethyl-4-methylphenyl) malonamide.

Example 16: Preparation of 2-(2,6-diethyl-4-methylphenyl) Malonamide

To a 100 mL three-necked flask equipped with a magnetic stirrer and a thermometer were sequentially added 3.6 g of water and 50.0 g of concentrated sulfuric acid. The reaction mixture was mixed and heated to 45° C., and 2-(2,6-diethyl-4-methylphenyl) malononitrile prepared in Example 14 was slowly added. The reaction mixture was reacted at 50° C. under stirring for 5 h. After the reaction was completed, the reaction mixture was cooled, poured into ice water, and subjected to extraction with ethyl acetate. The organic phases were combined, dried and concentrated to give 24.0 g of 2-(2,6-diethyl-4-methylphenyl) malonamide.

Example 17: Preparation of Pinoxaden

To a 250 mL three-necked flask equipped with a magnetic stirrer, a thermometer and a reflux condenser were sequentially added 24.8 g of 2-(2,6-diethyl-4-methylphenyl) malonamide prepared in Example 15, 21.0 g of [1,4,5]-oxadiazepine dihydrochloride, 125.0 g of chlorobenzene and 40.4 g of triethylamine. The reaction mixture was refluxed for reaction. After the reaction was complete, the reaction mixture was cooled to room temperature, and 21.6 g of pivaloyl chloride was slowly added, and reacted at room temperature under stirring for 2 h. Then the reaction mixture was adjusted with diluted hydrochloric acid to pH 3-4, and subjected to extraction with ethyl acetate. The organic phases were combined, dried, concentrated and crystallized with hexane to give 29.6 g of Pinoxaden.

$^1$H NMR (CDCl$_3$, 500 MHz, TMS): 68.88 (s, 2H), 4.28-4.26 (m, 2H), 3.94-3.93 (m, 2H), 3.89-3.83 (m, 4H), 2.56-2.47 (m, 2H), 2.45-2.40 (m, 2H), 2.39 (s, 3H), 1.12 (t, J=9.0 Hz, 3H), 1.23 (s, 9H).

Example 18: Preparation of Pinoxaden

To a 250 mL three-necked flask equipped with a magnetic stirrer, a thermometer and a reflux condenser were sequentially added 24.8 g of 2-(2,6-diethyl-4-methylphenyl) malonamide prepared in Example 16, 21.0 g of [1,4,5]-oxadiazepine dihydrochloride, 125.0 g of chlorobenzene and 40.4 g of triethylamine. The reaction mixture was refluxed for reaction. After the reaction was complete, the reaction mixture was cooled to room temperature, 21.6 g of pivaloyl chloride was slowly added and reacted at room temperature for 2 h. Then the reaction mixture was adjusted with diluted hydrochloric acid to pH 3-4, and subjected to extraction with ethyl acetate. The organic phases were combined, dried, concentrated and crystallized with hexane to give 29.7 g of Pinoxaden.

What is claimed is:

1. A conjugated triene compound of formula (1)

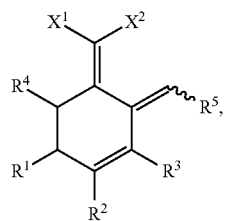

wherein $R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen and sulfur; and
$X^1$ and $X^2$ each are independently a cyano group or —COR$^6$ where R$^6$ is hydrogen, a $C_1$-$C_{10}$ alkyl group, a $C_1$-$C_{10}$ alkoxy group, a $C_6$-$C_{12}$ aryloxy group, an amino group, a $C_1$-$C_{10}$ alkylamino group, a $C_6$-$C_{12}$ arylamino group, a di($C_1$-$C_{10}$ alkyl) amino group, a ($C_1$-$C_{10}$ alkyl)($C_6$-$C_{12}$ aryl)amino group, a di($C_6$-$C_{12}$ aryl)amino group, a $C_6$-$C_{12}$ aryl group or a heteroaryl group containing one or two atoms selected from nitrogen, oxygen and sulfur.

2. The conjugated triene compound of claim 1, wherein $R^1$, $R^2$, $R^3$, $R^4$ and $R^5$ each are independently hydrogen, a $C_1$-$C_4$ alkyl group or a $C_6$-$C_{12}$ aryl group; and $X^1$ and $X^2$ each are independently a cyano group, —COOMe, —COOEt or —CONH$_2$.

3. The conjugated triene compound of claim 2, wherein $R^1$ and $R^3$ are hydrogen; $R^2$ and $R^5$ are methyl; and $R^4$ is ethyl.

4. A method for preparing a conjugated triene compound of formula (1), comprising:
subjecting compound (2) to isomerization to produce compound (3); and
subjecting the compound (3) to halogenation in the presence of a halogenating agent and dehydrohalogenation to produce the conjugated triene compound of formula (1), as shown in the following reaction scheme:

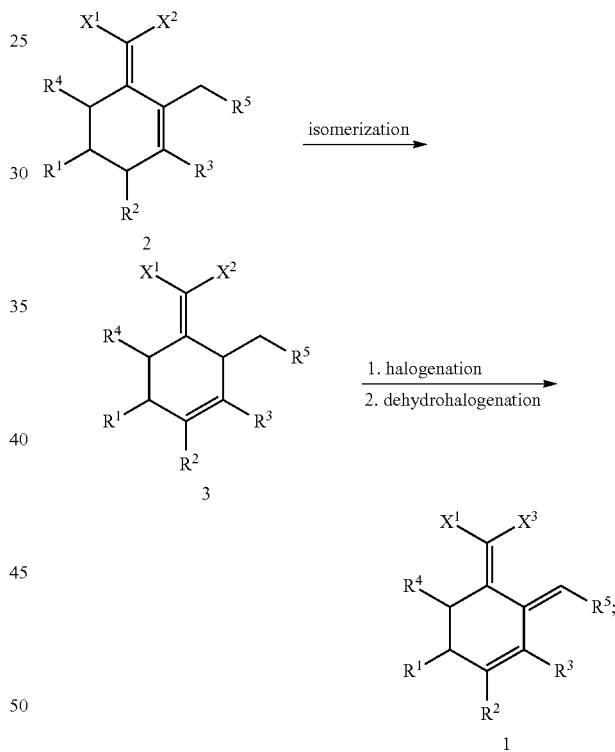

wherein:
$R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen and sulfur; and
$X^1$ and $X^2$ each are independently a cyano group or —COR$^6$ where R$^6$ is hydrogen, a $C_1$-$C_{10}$ alkyl group, a $C_1$-$C_{10}$ alkoxy group, a $C_6$-$C_{12}$ aryloxy group, an amino group, a $C_1$-$C_{10}$ alkylamino group, a $C_6$-$C_{12}$ arylamino group, a di($C_1$-$C_{10}$ alkyl) amino group, a ($C_1$-$C_{10}$ alkyl)($C_6$-$C_{12}$ aryl) amino group, a di($C_6$-$C_{12}$ aryl) amino group, a $C_6$-$C_2$ aryl group or a heteroaryl group containing one or two atoms selected from nitrogen, oxygen and sulfur.

5. The method of claim 4, wherein the isomerization is carried out in the presence of a base A; the base A is selected from the group consisting of an alkali metal hydroxide, an alkali metal alcoholate, an alkali metal hydride, an alkaline earth metal hydroxide, an alkaline earth metal alcoholate, an alkaline earth metal hydride and a mixture thereof; a molar ratio of the base A to the compound (2) is (0.8-2.4):1; the halogenating agent is selected from the group consisting of an elemental halogen, a hypohalous acid, a sulfonyl halide, a thionyl halide and a mixture thereof; and the dehydrohalogenation is performed at 0-100° C.

6. The method of claim 5, wherein the base A is sodium hydroxide or sodium methoxide; the molar ratio of the base A to the compound (2) is (1.0-1.2):1; the halogenating agent is chlorine gas, sulfonyl chloride or liquid bromine; and the dehydrohalogenation is performed at 50-80° C.

7. The method of claim 4, wherein the method is carried out in a one-pot manner.

8. A method of preparing a 2-aryl malonic acid derivative of formula (4), comprising:
aromatizing compound (1) to produce the 2-aryl malonic acid derivative (4), as shown in the following reaction scheme:

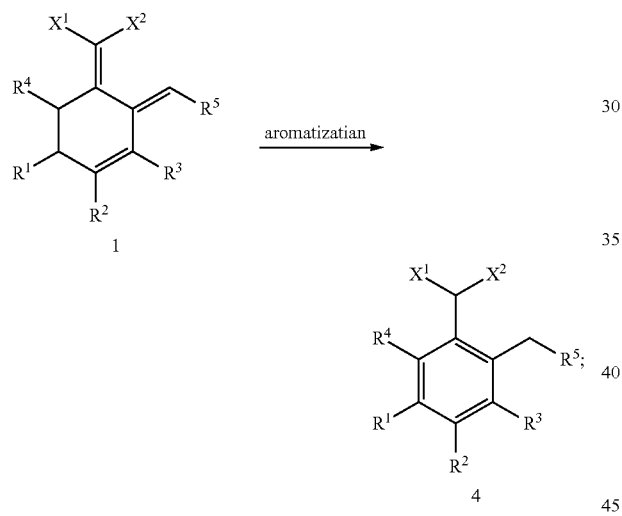

wherein:
$R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen or sulfur; and $X^1$ and $X^2$ each are independently a cyano group or —$COR^6$ where $R^6$ is hydrogen, a $C_1$-$C_{10}$ alkyl group, a $C_1$-$C_{10}$ alkoxy group, a $C_6$-$C_{12}$ aryloxy group, an amino group, a $C_1$-$C_{10}$ alkylamino group, a $C_6$-$C_{12}$ arylamino group, a di($C_1$-$C_{10}$ alkyl) amino group, a ($C_1$-$C_{10}$ alkyl)($C_6$-$C_2$ aryl) amino group, a di($C_6$-$C_2$ aryl) amino group, a $C_6$-$C_2$ aryl group or a heteroaryl group containing one or two atoms selected from nitrogen, oxygen and sulfur.

9. The method of claim 8, wherein $R^1$, $R^2$, $R^3$, $R^4$ and $R^5$ each are independently hydrogen, a $C_1$-$C_4$ alkyl group or a $C_6$-$C_{12}$ aryl group; and $X^1$ and $X^2$ each are independently a cyano group, —COOMe, —COOEt or —$CONH_2$.

10. The method of claim 8, wherein an aromatization temperature is 100-150° C.; the aromatization is carried out in the presence of a catalyst; the catalyst is selected from the group consisting of an alkali metal halide, an alkaline earth metal halide and a mixture thereof; and a molar ratio of the catalyst to the compound (1) is (0.005-2.4):1.

11. The method of claim 8, wherein an intermediate in a preparation of the compound (1) is not separated; and the 2-aryl malonic acid derivative (4) is obtained in a one-pot manner.

12. A method of synthesizing 2,2-dimethyl-,8-(2,6-diethyl-4-methylphenyl)-1,2,4,5-tetrahydro-7-oxo-7H-pyrazolo[1,2-d][1,4,5]oxadiazepin-9-yl ester, comprising:
aromatizing 2-(2,6-diethyl-4-methyl-3-ene-1-cyclohexylidene)malononitrile sequentially to obtain 2-(2,6-diethyl-4-methylphenyl) malononitrile;
reacting the 2-(2,6-diethyl-4-methylphenyl) malononitrile in the presence of concentrated sulfuric acid to obtain 2-(2,6-diethyl-4-methylphenyl) malonamide; and
subjecting the 2-(2,6-diethyl-4-methylphenyl) malonamide, [1,4,5]-oxadiazepine dihydrochloride and pivaloyl chloride to reaction in the presence of triethylamine to obtain 2,2-dimethyl-,8-(2,6-diethyl-4-methylphenyl)-1,2,4,5-tetrahydro-7-oxo-7H-pyrazolo[1,2-d][1,4,5]oxadiazepin-9-yl ester, as shown in the following reaction scheme:

* * * * *